US005908825A

United States Patent [19]

Fasano et al.

[11] Patent Number: 5,908,825
[45] Date of Patent: Jun. 1, 1999

[54] DOSAGE COMPOSITION FOR NASAL DELIVERY AND METHOD OF USE OF THE SAME

[75] Inventors: Alessio Fasano, Ellicott City, Md.; Teresa De Magistris, Siena, Italy; Sergio Uzzau, Sassari, Italy; Rino Rappuoli, Querciegrossa, Italy

[73] Assignees: University of Maryland at Baltimore, Baltimore, Md.; Chiron S.p.A., Siena, Italy

[21] Appl. No.: 08/781,057

[22] Filed: Jan. 9, 1997

[51] Int. Cl.$^6$ ........................................................ A61K 9/14
[52] U.S. Cl. .................................... 514/2; 514/3; 514/12; 514/15; 424/130.1; 424/184.1; 424/261.1
[58] Field of Search ............................... 514/2, 3, 12, 15, 514/4, 866; 424/261.1, 130.1, 184.1; 530/303, 362, 351, 387.1, 399

[56] References Cited

U.S. PATENT DOCUMENTS

| | | | |
|---|---|---|---|
| 5,470,729 | 11/1995 | Kaper et al. | 424/93.2 |
| 5,665,389 | 9/1997 | Fasano | 424/464 |

FOREIGN PATENT DOCUMENTS

WO9637196  11/1996  WIPO .

OTHER PUBLICATIONS

Fasano et al., 'Vibrio Chlerae Produces a Second Entertoxin, Which Affects Intestinal Tight Junctions', vol. 88, pp. 5242–5246, Jun. 1991.
Kaper et al., 'CHOLERA', Clinical Microbiology Reviews, vol. 8, No. 1, pp. 48–61, Jan. 1995.
Werner et al., 'Development of Human Nasal Epithelial Cell Culutre Model and its Sutability for Transport and Metabolism Studies Under in vitro Conditions', Pharmaceutical Research, vol. 12, No. 4pp. 565–571, 1995.
Herard et al., 'Epithelial Barrier Integrity During in vitro Sound Repair of the Airway Epithelium', vol. 15, pp. 624–632, 1996.
Fiore et al, Gastroenterology, 110:A323 (1996).
Fasano et al, The Journal of Clinical Investigations, Inc., 96:710–720 (1995).
Di Tommaso et al, Infection and Immunity, 64(3):974–979 (1996).
Hochman et al, "Mechanism of Absorption Enhancement and Tight Junction Regulation", J. or Controlled Release, 29:253–267 (1994).
Fasano et al, Mechanism of Action of Zonula Occludens Toxin (ZOT) Elaborated by Vibrio cholerae, 29th Joint Conference on Cholera and Related Diarrheal Disease, p. 214 (1993).
Chapron et al, "Gastric Retention of Enteric–Coated Magnesium Chloride Tablets" Abstract, Annals of Pharmacotherapy, 28(7–8):874–877 (1994).
Digenis et al, "Cross–Linking of Gelatin Capsules and Its Relevance to Their In Vitro–In Vivo Performance", Abstract, J. of Pharmaceutical Sciences, 83(7):915–921 (1994).

Vantini et al, In Vitro Study of a New Pancreatic Enzyme with High Lipase Content in Enteric Coated Microtablets, Abstract, Clinica Terapeutica, 142(5):445–451 (1993).
Yoshitomi et al, "Evaluation of Enteric Coated Tablet Sensitive to Pancreatic Lipase", Abstract, Chemical and Pharmaceutical Bulletin, 40(7):1902–1905 (1992).
Thoma et al, "The Solubility Kinetics of Enteric–Resistant Tablets Using Riboflavin Test Tablets. 6. Pharmaceutic–Technologic and Analytic Studies on Gastric Juice–Resistant Dosage Forms", Abstract, Pharmazie, 46(5):331–336 (1991).
Morishita et al, "Controlled Release Microspheres Based on Eudragit L100 for the Oral Administration of Erythromycin", Abstract, Drug Design and Delivery, 7(4):309–319 (1991).
Lin et al, "Tablet Formulation Study of Spray–dried Sodium Diclofenac Enteric–Coated Microcapsules", Abstract, Pharmaceutical Research, 8(7):919–924 (1991).
Hardy et al, "Evaluation of an Enteric and Therapeutics", Abstract, Alimentary Pharmacology and Therapeutics, 5(1):69–75 (1991).
Fasano et al, Mechanism of Action of Zonula Occludens (ZOT) Elaborated by Vibrio cholerae, Abstract (B–13), p. 31, 94th ASM General Meeting (May 23–27, 1994).
Fasano et al, Regulation of Intestinal Tight Junctions By Zonula Occludens Toxin (ZOT) Elaborated by Vibrio cholerae, Abstract, Clinical Research, 42(2):286A (1994).
Fasano et al, Mechanism of Action of Zonula Occludens Toxin (ZOT) Elaborated by Vibrio cholerae, Abstract (1060), Pediatrica Research, 35 (4/2):179A (1994).
Fasano et al, Mechanism of Action of Zonula Occludens Toxin (ZOT) Elaborated by Vibrio Cholerae, Abstract, Gastroenterology, 106(4):A232 (1994).
Kasper et al, "Cholera", Clinical Microbiology Reviews, 8(1):48–86 (1995).
Levine, "Current Status of Vaccine Development for Enteric Diseases", Seminars in Pediatric Infectious Diseases, 5(3):243–250 (1994).
Guandalini et al "Gli Enterovaccini" Febbre Enterica, pp. 109–121.
Guandalini et al, "Acute Infectious Diarrhoea", Management of Digestive and Liver Disorders In Infants and Children, pp. 319–349 (1993).
Fasano et al, Vibrio cholerae Produces a Second Enterotoxin, Which Affects Intestinal Tight Junctions, Proc. Natl. Acad. Sci. USA, 88:5242–5246 (1991).
Baudry et al, "Cloning of a Gene (zot) Encoding a New Toxin Produced by Vibrio cholerae", Infection and Immunity, 60(2):428–434 (1992).
Leong et al, "Identification of the Integrin–Binding Domain of the Yersinia pseudotuberculosis Invasin Protein", The EMBO Journal, 9(6):1979–1989 (1990).

Primary Examiner—Cecilia J. Tsang
Assistant Examiner—Anish Gupta
Attorney, Agent, or Firm—Sughrue, Mion, Zinn Macpeak & Seas, PLLC

[57] ABSTRACT

A nasal dosage composition for nasal delivery comprising (A) a therapeutic agent; and (B) zonula occludens toxin, as well as a method for the use of the same.

32 Claims, 4 Drawing Sheets

SEQUENCE LISTING (1) GENERAL INFORMATION:

(iii) NUMBER OF SEQUENCES: 2

(2) INFORMATION FOR SEQ ID NO:1:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:1:

TCATCACGGC GCGCCAGG                                                   18

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:2:

GGAGGTCTAG AATCTGCCCG AT                                              22
```

DOSAGE COMPOSITION FOR NASAL DELIVERY AND METHOD OF USE OF THE SAME

The development of the present invention was supported by the University of Maryland, Baltimore, Md.

FIELD OF THE INVENTION

The present invention relates to a nasal dosage composition for nasal delivery comprising (A) a therapeutic agent; and (B) a nasal absorption enhancing effective amount of zonula occludens toxin, as well as a method for the use of the same.

BACKGROUND OF THE INVENTION

I. Nasal Delivery Systems

Until recently, antibiotics, anti-inflammatory steroids and decongestants have been administered intranasally only for their local action, e.g., nasal decongestion and bronchodilation. The observation that systemic side-effects appeared in some cases led to the conclusion that the nasal mucosa permits the systemic availability of some drugs. Nasal delivery offers promising alternative to parenteral administration of therapeutic agents that cannot tolerate the rigorous gastrointestinal environment after oral administration. Nasal administration may therefore be considered as one of the possible alternatives to delivering peptides and protein drugs.

The primary function of the nose is olfaction, but it also filters airborne particulates, as well as heat and humidified inspired air. In adult humans, the nasal cavities are covered by a 2.0 to 4.0 mm thick mucosa (Mygind, *Nasal Allergy*, Blackwell Scientific, Oxford (1979)). The volume of the nasal cavity is about 20 ml, and its total surface area is about 180 cm$^2$ (Schreider, *Toxicology of the Nasal Passage*, Hemisphere, Washington, D.C., pages 1–23 (1986)). Absorption of therapeutic agents across the nasal mucosa results in direct systemic exposure, thus avoiding the first-pass hepatic metabolism associated with oral administration. However, an alternative first-pass effect is created by the metabolic activity within the nasal mucosa (Sarkar, *Pharmacol. Res.*, 9:1–9 (1992)).

Although the bioavailability of peptides and proteins from the nasal mucosa is substantially improved over the oral route, it is still far from optimal when compared to the intravenous route. This limitation may be attributed to the resistance encountered by macromolecules in penetrating the nasal mucosa through the paracellular pathway (Sackar, supra).

Studies on the use of the paracellular pathway have not been extensively explored, mainly because of lack of information on tight junctions (tj) structure and function. That is, entry of molecules through the paracellular pathway is primarily restricted by the tj (Gumbiner, *Am. J. Physiol.*, 253:C749–C758 (1987); and Madara, *J. Clin. Invest.*, 83:1089–1094 (1989)).

In transmission electron microscopy, tj appear as an approximately 80 nm long region at the boundary of neighboring cells in which the plasma membranes of adjacent cells are brought into close opposition (Farquhar et al,*J. Cell Biol.*, 17:375–412 (1963)). This structure circumscribes epithelial cells immediately below the apical domain, forming a seal between epithelial cells and their neighbors. This seal restricts diffusion of small molecules in a charge specific manner (Pappenheimer et al, *J. Membrane Biol.*, 102:2125–2136 (1986) ; Madara et al, *J. Cell Biol.*, 102:2125–2136 (1986); Claude et al, *J. Cell Biol.*, 58:390–400 (1973); and Bakker et al, *J. Membrane Biol.*, 11:25–35 (1989)), and completely occludes molecules with molecular radii larger then 11 Å (Madara et al,*J. Cell Biol.*, 98:1209–1221 (1985)). Thus, considerable attention has been directed to finding ways to increase paracellular transport by "loosening" tj.

To overcome the poor uptake from the nasal mucosa, absorption enhancers are employed in attempts to increase the extent of peptide absorption. Examples of these enhancers include bile salts (Duchateau et al, *Int. J. Pharm.* 31:193–196 (1986)), chelating agents (Lee, *In: Delivery Systems for Peptide Drugs*, Plenum, New York, pages 87–104 (1986)), and surfactants (Hirai et al, *Int. J. Pharm.* 9:165–169 (1981)). Since the penetration enhancers listed above promote peptide and protein absorption by perturbing membrane integrity, it is inevitable that varying extents of insult will occur to the mucosal tissues that are in contact with the enhancer (Lee, supra). The alteration of the membrane integrity can permanently damage the nasal membrane (Hirai et al, supra) and, consequently, makes the use of these substances unacceptable for chronic treatments in humans.

Thus, there has been a desire in the art to develop nasal absorption enhancers which do not have the above-discussed limitations.

II. Function and Regulation of Tight Junctions

The tj or zonula occludens (hereinafter "ZO") are one of the hallmarks of absorptive and secretory epithelia (Madara, *J. Clin. Invest.*, 83:1089–1094 (1989); and Madara, *Textbook of Secretory Diarrhea* Eds. Lebenthal et al, Chapter 11, pages 125–138 (1990). As a barrier between apical and basolateral compartments, they selectively regulate the passive diffusion of ions and water-soluble solutes through the paracellular pathway (Gumbiner,*Am. J. Physiol.*, 253 (Cell Physiol. 22):C749–C758 (1987)). This barrier maintains any gradient generated by the activity of pathways associated with the transcellular route (Diamond, *Physiologist*, 20:10–18 (1977)).

Variations in transepithelial conductance can usually be attributed to changes in the permeability of the paracellular pathway, since the resistances of cell plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, *J. Cell Biol.*, 101:2124–2133 (1985)).

There is abundant evidence that ZO, once regarded as static structures, are in fact dynamic and readily adapt to a variety of developmental (Magnuson et al, *Dev. Biol.*, 67:214–224 (1978); Revel et al, *Cold Spring Harbor Symp. Quant. Biol.*, 40:443–455 (1976); and Schneeberger et al,*J. Cell Sci.*, 32:307–324 (1978)), physiological (Gilula et al, *Dev. Biol.*, 50:142–168 (1976); Madara et al, *J. Membr. Biol.*, 100:149–164 (1987); Mazariegos et al, *J. Cell Biol.*, 98:1865–1877 (1984); and Sardet et al, *J. Cell Biol.*, 80:96–117 (1979)), and pathological (Milks et al, *J. Cell Biol.*, 103:2729–2738 (1986); Nash et al, *Lab. Invest.*, 59:531–537 (1988); and Shasby et al, *Am. J. Physiol.*, 255(*Cell Physiol.*, 24):C781–C788 (1988)) circumstances. The regulatory mechanisms that underlie this adaptation are still not completely understood. However, it is clear that, in the presence of Ca$^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist,* 20:10–18 (1977)). A candidate for the transmembrane protein strands, occludin, has been identified (Furuse et al, *J. Membr. Biol.,* 87:141–150 (1985)).

Six proteins have been identified in a cytoplasmic submembranous plague underlying membrane contacts, but their function remains to be established (Diamond, supra). ZO-1 and ZO-2 exist as a heterodimer (Gumbiner et al, *Proc. Natl. Acad. Sci., USA,* 88:3460–3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.,* 83:129–145 (1988)). Two other proteins, cingulin (Citi et al, *Nature* (London), 333:272–275 (1988)) and the 7H6 antigen (Zhong et al, *J. Cell Biol.,* 120:477–483 (1993)) are localized further from the membrane and have not yet been cloned. Rab 13, a small GTP binding protein has also recently been localized to the junction region (Zahraoui et al, *J. Cell Biol.,* 124:101–115 (1994)). Other small GTP-binding proteins are known to regulate the cortical cytoskeleton, i.e., rho regulates actin-membrane attachment in focal contacts (Ridley et al, *Cell,* 70:389–399 (1992)), and rac regulates growth factor-induced membrane ruffling (Ridley et al, *Cell,* 70:401–410 (1992)). Based on the analogy with the known functions of plaque proteins in the better characterized cell junctions, focal contacts (Guan et al, *Nature,* 358:690–692 (1992)), and adherens junctions (Tsukita et al, *J. Cell Biol.,* 123:1049–1053 (1993)), it has been hypothesize that tj-associated plague proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.,* 107:1037–1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS") MARCKS is a specific protein kinase C (hereinafter "PKC") substrate that is associated with the cytoplasmic face of the plasma membrane (Aderem, *Elsevier Sci. Pub.* (UK), pages 438–443 (1992)). In its non-phosphorylated form, MARCKS crosslinks to the membrane actin. Thus, it is likely that the actin meshwork associated with the membrane via MARCKS is relatively rigid (Hartwig et al, *Nature,* 356:618–622 (1992)). Activated PKC phosphorylates MARCKS, which is released from the membrane (Rosen et al, *J. Exp. Med.,* 172:1211–1215 (1990); and Thelen et al, *Nature,* 351:320–322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra), These data suggest that the F-actin network may be rearranged by a PKC-dependent phosphorylation process that involves actin-binding proteins (MARCKS being one of them).

A variety of intracellular mediators have been shown to alter tj function and/or structures. Tight junctions of amphibian gallbladder (Duffey et al, *Nature,* 204:451–452 (1981)), and both goldfish (Bakker et al, *Am. J. Physiol.,* 246:G213–G217 (1984)) and flounder (Krasney et al, *Fed. Proc.,* 42:1100 (1983)) intestine, display enhanced resistance to passive ion flow as intracellular cAMP is elevated. Also, exposure of amphibian gallbladder to $Ca^{2+}$ ionophore appears to enhance tj resistance, and induce alterations in tj structure (Palant et al, *Am. J. Physiol.,* 245:C203–C212 (1983)). Further, activation of PKC by phorbol esters increases paracellular permeability both in kidney (Ellis et al *C. Am. J. Physiol.,* 263 (*Renal Fluid Electrolyte Physiol.* 32):F293–F300 (1992)), and intestinal (Stenson et al, *C. Am. J. Physiol.,* 265(*Gastrointest. Liver Physiol.,* 28):G955–G962 (1993)) epithelial cell lines.

III. Zonula Occludens Toxin

Most *Vibrio cholerae* vaccine candidates constructed by deleting the ctxA gene encoding cholera toxin (CT) are able to elicit high antibody responses, but more than one-half of the vaccinees still develop mild diarrhea (Levine et al, *Infect. Immun.,* 56(1):161–167 (1988)). Given the magnitude of the diarrhea induced in the absence of CT, it was hypothesized that *V. cholerae* produce other enterotoxigenic factors, which are still present in strains deleted of the ctxA sequence (Levine et al, supra). As a result, a second toxin, zonula occludens toxin (hereinafter "ZOT") elaborated by *V. cholerae* and which contribute to the residual diarrhea, was discovered (Fasano et al, *Proc. Nat. Acad. Sci., USA* 8:5242–5246 (1991)). The zot gene is located immediately adjacent to the ctx genes. The high percent concurrence of the zot gene with the ctx genes among *V. cholerae* strains (Johnson et al, *J. Clin. Microb.,* 31/3:732–733 (1993), and Karasawa et al, *FEBS Microbiology Letters,* 106:143–146 (1993)) suggests a possible synergistic role of ZOT in the causation of acute dehydrating diarrhea typical of cholera. Recently, the zot gene has also been identified in other enteric pathogens (Tschape, 2nd *Asian-Pacific Symposium on Typhoid fever and other Salomellosis,* 47(Abstr.) (1994)).

It has been previously found that, when tested on rabbit ileal mucosa, ZOT increases the intestinal permeability by modulating the structure of intercellular tj (Fasano et al, supra). It has been found that as a consequence of modification of the paracellular pathway, the intestinal mucosa becomes more permeable. It also was found that ZOT does not affect $Na^+$-glucose coupled active transport, is not cytotoxic, and fails to completely abolish the transepithelial resistance (Fasano et al, supra).

More recently, it has been found that ZOT is capable of reversibly opening tj in the intestinal mucosa, and thus ZOT, when co-administered with a therapeutic agent, is able to effect intestinal delivery of the therapeutic agent, when employed in an oral dosage composition for intestinal drug delivery (WO 96/37196; U.S. patent application Ser. No. 08/443,864, filed May 24, 1995; and U.S. patent application Ser. No. 08/598,852, filed Feb. 9, 1996; each of which is incorporated by reference herein in their entirety).

In the present invention, it has been demonstrated, for the first time, that ZOT, when co-administered with a therapeutic agent, is able to enhance nasal absorption of a therapeutic agent. This finding was unexpected for the following reasons:

(1) *Vibrio cholera* naturally infect the intestinal mucosa, not the nasal mucosa;

(2) The effect of ZOT on the intestinal mucosa is not uniform, i.e., ZOT exhibits its permeablizing effect only on the small intestine, not on the large intestine; and (3) The regional effect of ZOT appears to be related to the distribution of its receptor within the intestine, i.e., the receptor is expressed only by mature cells on the tip of the villi in the jejunum and ileum. It is not present on the surface of colonocytes (Fiore et al, *Gastroenterology,* 110:A323 (1996)). Heretofore, it was not known whether the ZOT receptor was expressed on the surface of nasal mucosa.

Thus, there was no reasonable expectation that a *Vibrio cholera* toxin, e.g., ZOT, would have any effect on tj of the nasal epithelia.

SUMMARY OF THE INVENTION

An object of the present invention is to provide nasal absorption enhancers which rapidly open tj in a reversible and reproducible manner.

Another object of the present invention is to provide nasal absorption enhancers which can be used safely without damaging the nasal epithelium.

Still another object of the present invention is to provide an nasal dosage composition which allows for the systemic delivery of therapeutic agents.

Yet another object of the present invention is to provide a method for nasal delivery of therapeutic agents such that they are absorbed by the nasal mucosa.

These and other objects of the present invention, which will be apparent from the detailed description of the invention provided hereinafter, have been met in one embodiment by a nasal dosage composition for nasal delivery comprising:

(A) a therapeutic agent; and (B) a nasal absorption enhancing effective amount of zonula occludens toxin.

In another embodiment, the above-described objects of the present invention have been met by method for nasal delivery of a therapeutic agent comprising nasally administering a dosage composition for nasal delivery comprising:

(A) a therapeutic agent; and (B) a nasal absorption enhancing effective amount of zonula occludens toxin.

DETAILED DESCRIPTION OF THE INVENTION

As discussed above, in one embodiment, the present invention relates to a nasal dosage composition for nasal delivery comprising:

(A) a therapeutic agent; and (B) a nasal absorption enhancing effective amount of zonula occludens toxin.

Nasal dosage compositions for nasal delivery are well-known in the art. Such nasal dosage compositions generally comprise water-soluble polymers that have been used extensively to prepare pharmaceutical dosage forms (Martin et al, *In: Physical Chemical Principles of Pharmaceutical Sciences,* 3rd Ed., pages 592–638 (1983)) that can serve as carriers for peptides for nasal administration (Davis, *In: Delivery Systems for Peptide Drugs,* 125:1–21 (1986)). The nasal absorption of peptides embedded in polymer matrices has been shown to be enhanced through retardation of nasal mucociliary clearance (Illum et al, *Int. J. Pharm.,* 46:261–265 (1988)). Other possible enhancement mechanisms include an increased concentration gradient or decreased diffusion path for peptides absorption (Ting et al, *Pharm. Res.,* 9:1330–1335 (1992)). However, reduction in mucociliary clearance rate has been predicted to be a good approach toward achievement or reproducible bioavailability of nasally administered systemic drugs (Gonda et al, *Pharm. Res.,* 7:69–75 (1990)). Microparticles with a diameter of about 50 $\mu$m are expected to deposit in the nasal cavity (Bjork et al, *Int. J. Pharm.,* 62:187–192 (1990)); and Illum et al, *Int. J. Pharm.,* 39:189–199 (1987), while microparticles with a diameter under 10 $\mu$m can escape the filtering system of the nose and deposit in the lower airways. Microparticles larger than 200 $\mu$m in diameter will not be retained in the nose after nasal administration (Lewis et al, *Proc. Int. Symp. Control Rel. Bioact. Mater.,* 17:280–290 (1990)).

The particular water-soluble polymer employed is not critical to the present invention, and can be selected from any of the well-known water-soluble polymers employed for nasal dosage forms. A typical example of a water-soluble polymer useful for nasal delivery is polyvinyl alcohol (PVA). This material is swellable hydrophilic polymer whose physical properties depend on the molecular weight, degree of hydrolysis, cross-linking density, and crystallinity (Peppas et al, *In: Hydrogels in Medicine and Pharmacy,* 3:109–131 (1987)). PVA can be used in the coating of dispersed materials through phase separation, spray-drying, spray-embedding, and spray-densation (Ting et al, supra).

A "nasal" delivery composition differs from an "intestinal" delivery composition in that the latter must have gastroresistant properties in order to prevent the acidic degradation of the active agents (e.g., ZOT and the therapeutic agent) in the stomach, whereas the former generally comprises water-soluble polymers with a diameter of about 50 $\mu$m in order to reduce the mucociliary clearance, and to achieve a reproducible bioavalaibility of the nasally administered agents.

The particular therapeutic agent employed is not critical to the present invention, and can be, e.g., any drug compound, biologically active peptide, vaccine, or any other moiety otherwise not absorbed through the transcellular pathway, regardless of size or charge.

Examples of drug compounds which can be employed in the present invention include drugs which act on the cardiovascular system drugs which act on the central nervous system, antineoplastic drugs and antibiotics.

Examples of drugs which act on the cardiovascular system which can be employed in the present invention include lidocaine, adenosine, dobutamine, dopamine, epinephrine, norepinephrine and phentolamine.

Examples of drugs which act on the central nervous system which can be employed in the present invention include doxapram, alfentanil, dezocin, nalbuphine, buprenorphine, naloxone, ketorolac, midazolam, propofol, metacurine, mivacurium and succinylcholine.

Examples of antineoplastic drugs which can be employed in the present include cytarabine, mitomycin, doxorubicin, vincristine and vinblastine.

Examples of antibiotics which can be employed in the present include methicillin, mezlocillin, piperacillin, cetoxitin cefonicid, cefmetazole and aztreonam.

Examples of biologically active peptides which can be employed in the present invention include hormones, lymphokines, globulins, and albumins.

Examples of hormones which can be employed in the present invention include testosterone, nandrolene, menotropins, progesterone, insulin and urofolltropin.

Examples of lymphokines which can be employed in the present invention include interferon-α, interferon-β, interferon-γ, interleukin-1, interleukin-2, interleukin-4 and interleukin-8.

Examples of globulins which can be employed in the present invention include α-globulins, β-globulins and γ-globulins (immunoglobulin).

Examples of immunoglobulins which can be employed in the present invention include polyvalent IgG or specific IgG, IgA and IgM, e.g., anti-tetanus antibodies.

An example of albumin which can be employed in the present invention is human serum albumin and ovalbumin.

Examples of vaccines which can be employed in the present invention include peptide antigens and attenuated microorganisms and viruses.

Examples of peptide antigens which can be employed in the present invention include the B subunit of the heat-labile enterotoxin of enterotoxigenic *E. coli,* the B subunit of cholera toxin, capsular antigens of enteric pathogens, fimbriae or pili of enteric pathogens, HIV surface antigens, dust allergens and acari allergens.

Examples of attenuated microorganisms and viruses which can be employed in the present invention include those of enterotoxigenic *Escherichia coli,* enteropathogenic *Escherichia coli, Vibrio cholerae, Shigella flexneri, Salmonella typhi, Helicobacter pylori* and rotavirus (Fasano et al; *In: Le Vaccinazioni in Pediatria,* Eds. Vierucci et al, CSH, Milan, pages 109–121 (1991); Guandalini et al, *In: Management of Digestive and Liver Disorders in Infants and Children,* Elseviore Eds. Butz et al, Amsterdam, Chapter 25 (1993); Levine et al, *Sem. Ped. Infect. Dis.,* 5:243–250 (1994), Kaper et al, *Clin. Micrbiol. Rev.,* 8:48–86 (1995); and MacArthur et al, *JAMA,* 273:729–734 (1995), each of which is incorporated by reference herein in its entirety).

When the therapeutic agent is insulin, the nasal dosage composition of the present invention is useful for the treatment of diabetes.

The amount of therapeutic agent employed is not critical to the present invention and will vary depending upon the particular agent selected, the disease or condition being treated, as well as the age, weight and sex of the subject being treated.

The amount of zonula occludens toxin (hereinafter "ZOT") employed is also not critical to the present invention and will vary depending upon the age, weight and sex of the subject being treated. Generally, the final concentration of ZOT employed in the present invention to enhance absorption of the therapeutic agent by the nose is in the range of about $10^{-5}$ M to $10^{-10}$ M, preferably about $10^{-6}$ M to $5.0 \times 10^{-8}$ M. To achieve such a final concentration in the nose, the amount of ZOT in a single nasal composition of the present invention will generally be about 40 ng to 1000 ng, preferably about 400 ng to 800 ng.

The ratio of therapeutic agent to ZOT employed is not critical to the present invention and will vary depending upon the amount of therapeutic agent to be delivered within the selected period of time. Generally, the weight ratio of therapeutic agent to ZOT employed in the present invention is in the range of about 1:10 to 3:1, preferably about 1:5 to 2:1.

ZOT is produced by *V. cholerae.* The particular strain of *V. cholera* from which ZOT is derived is not critical to the present invention. Examples of such *V. cholerae* strains include strain 569B, 395 and E7946 (Levine et al, supra; Johnson et al, supra; and Karasawa et al, supra).

As used herein, "ZOT" refers to the mature protein of 399 amino acids, as well as mutants thereof which retain the ability to regulate tj. For example, an N-terminal deletion of amino acids 1–8 can be made without effecting ZOT activity, and N-terminal fusion proteins of ZOT can be made without effecting ZOT activity. Such mutants can be readily prepared by site-directed mutagenesis, and screened for ZOT activity as described herein.

ZOT can be obtained and purified, e.g., by genetically-engineered *E. coli* strains overexpressing the zot gene (Baudry et al, *Infect. Immun.,* 60:428–434 (1992)), alone or fused to other genes, such as maltose binding protein (see Example 1 below) or glutathione-s-transferase (see Example 2 below).

The following examples are provided for illustrative purposes only, and are in no way intended to limit the scope of the present invention.

EXAMPLE 1

Preparation and Purification of ZOT and MBP-ZOT and GST-ZOT

Preparation and Purification of ZOT

A $M_r$>10,000 supernatant fraction containing ZOT was obtained after culturing *V. cholerae* strain CVD110 transformed with plasmid pZ14 (hereinafter "pZ14 supernatant").

CVD110 is a *V. cholerae* (El Tor biotype) strain in which all known toxin genes (ctxA, zot and ace genes) have been deleted (Michalski et al, *Infect. Immun.,* G1:4462–4468 (1993)).

Plasmid pZ14 contains the zot gene transcribed by the inducible tac promoter. Plasmid pZ14 was constructed by digesting pBB241 with HindIII. pBB241 was obtained by cloning a ClaI-XbaI fragment containing the entire zot sequence into plasmid pUC19 (Baudry et al, supra). The 5' overhang was filled in with Klenow fragment, and the linearized plasmid was digested with XbaI, yielding a zot fragment of 1.5 kb. This fragment was cloned into vector pTTQ181 (Amersham, Arlington Heights, Ill.) which was modified by interruption of the $Amp^R$ gene by the $Kan^R$ cassette found in pHSG274 described in Maniatis et al, *Molecular Cloning, A Laboratory Manual,* Cold Spring Harbor (1989). That is, pTTQ181 was digested with EcoRI, filled in, and digested with XbaI. The 1.5 kb XbaI zot fragment was ligated into the resulting vector in the correct orientation, and was designated "pZ14".

The $M_r$>10,000 supernatant fraction was prepared as follows. CVD110 transformed with pZ14 was cultured overnight at 37° C., in Luria Bertani (hereinafter "LB") broth containing 50 μg/ml kanamycin so as to select kanamycin-resistant strains harboring pZ14 plasmid. The cultures were then diluted to obtain an initial OD 600 nm of 0.4–0.5. Next, to induce expression of ZOT from the tac promoter, 2.0 mM of Isopropyl-Thio-β-D-Galactopyranoside (IPTG) (5'-3'

Incorporation, Boulder, Colo.) was added to the cultures, which were incubated at 37° C. for another 2 hr. Next, the culture medium was collected, cooled and centrifuged at 5,000×g for 10 min at 4° C. The resulting liquid was collected and passed through a 0.45 μm filter (Millipore). The resulting culture supernatant was then subjected to ultrafiltration through Centricon filters (Vangard International Corp., N.J.) with a 10 kDa M cut-off size. The $M_r$>10 kDa fraction was washed twice with phosphate buffered saline (pH 7.4) (hereinafter "PBS"), reconstituted to the original volume in PBS.

5000 ml of the resulting pZ14 supernatant was then concentrated 1000-fold using a lamina flow filter with a NW cutoff of 10 kDa, and then subjected to 8.0% (w/v) SDS-PAGE. Protein bands were detected by Coomassie blue staining of the SDS-PAGE gel. No protein band corresponding to ZOT was detectable when compared to control pTTQ181 supernatant treated in the same manner. Therefore, even though the zot gene was placed behind the highly inducible and strong tac promoter in pZ14, the level of the protein in 1000-fold concentrated pZ14 supernatant was still not detectable by the Coomassie stained SDS-PAGE gel.

B. Preparation and Purification of MBP-ZOT

To increase the amount of ZOT produced, the zot gene was fused in frame with the maltose binding protein (hereinafter "MBP") gene to create a MBP-ZOT fusion protein.

The MBP vector pMAL-c2 (Biolab) was used to express and purify ZOT by fusing the zot gene to the malE gene of *E. coli*. This construct uses the strong, inducible tac promoter, and the malE translation initiation signals to give high level expression of the cloned zot gene. The vector pMAL-c2 has an exact deletion of the malE signal sequence, which leads to cytoplasmic expression of the fusion protein. Affinity chromatography purification for MBP was used to facilitate isolation of the fusion protein (Biolab).

More specifically, vector pMAL-c2 was linearized with EcoRI (that cuts at the 3' end of the malE gene) filled in with Klenow fragment, and digested with XbaI (that has a single site in pMAL-c2 polylinker). The orf encoding ZOT was subcloned from plasmid pBB241 (Baudry et al, supra). Plasmid pBB241 was digested with BssHII, filled in with Klenow fragment, and digested with XbaI. Then, the blunt-XbaI fragment was subcloned into pMAL-c2 to give plasmid pLC10-c. Since both the insert, and the vector had blunt and sticky ends, the correct orientation was obtained with the 3' end of malE fused with the 5' terminus of the insert. pLC10-c was then electroporated into *E. coli* strain DH5α. In pBB241, the BssHII restriction site is within the zot orf. Thus, amino acids 1–8 of ZOT are missing in the MBP-ZOT fusion protein.

In order to purify the MBP-ZOT fusion protein, 10 ml of Luria Bertani broth containing 0.2% (w/v) glucose and 100 μg/ml ampicillin were inoculated with a single colony containing pLC10-c, and incubated overnight at 37° C. with shaking. The culture was diluted 1:100 in 1.0 l of the same fresh medium, and grown at 37° C. while shaking, to about 1.0×10⁸ cells/ml. 0.2 mM IPTG was then added to induce the MBP-ZOT expression, and the culture was incubated at 37° C. for additional 3 hr. The bacteria were then pelleted and resuspended in 20 ml of ice cold "column buffer" comprising 20 mM Tris-HCl 0.2 M NaCl, 1.0 mM EDTA, 10 mM 2-ME, 1.0 mM $NaN_3$. The bacterial suspension was lysed by french press treatment and spun for 30 min at 13,000×g at 4° C. The supernatant was collected, diluted 1:5 with column buffer and loaded into a 1×10 column of amylose resin (Biolabs, MBP-fusion purification system), pre-equilibrated with column buffer. After washing the column with 5 volumes of column buffer, the MBP-ZOT fusion protein was eluted by loading 10 ml of 10 mM maltose in column buffer. The typical yield from 1.0 l of culture was 2–3 mg of protein.

The MBP fusion partner of the purified MBP-ZOT fusion protein was then cleaved off using 1.0 μg of Factor Xa protease (Biolabs) per 20 μg of HBP-ZOT. Factor Xa protease cleaves just before the amino terminus of ZOT. The ZOT protein so obtained was run on a 8.0% (w/v) SDS-PAGE gel, and electroeluted from the gel using an electroseparation chamber (Schleicher & Schuell, Keene, N.H.).

Figure 3:
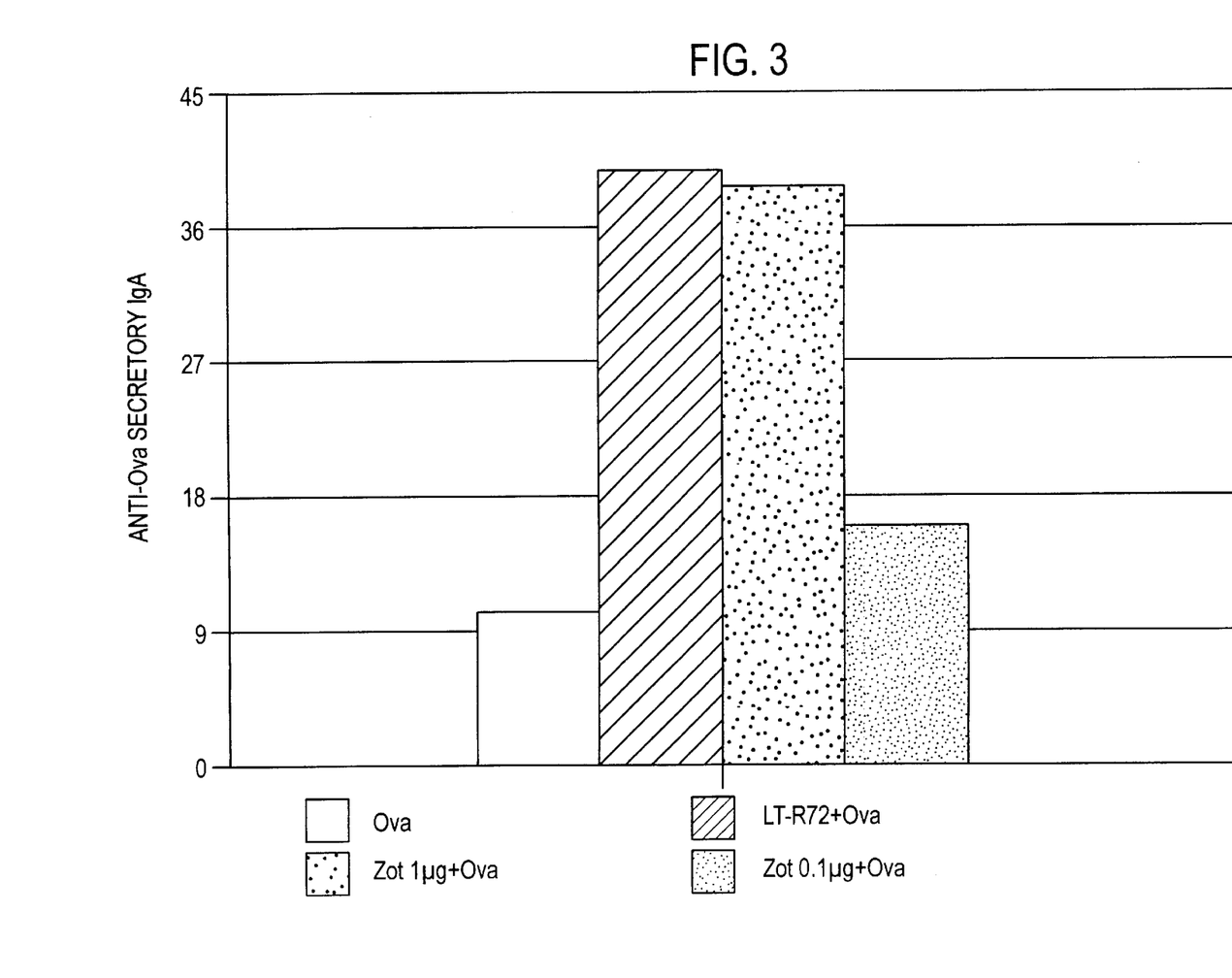
FIG. 3 shows the anti-Ova secretory IgA antibodies in the nasal wash of mice treated with Ova alone (open bars), LT-R72+Ova (hatched bars), and ZOT+Ova (shaded bars).

When tested in Ussing chambers, the resulting purified ZOT induced a dose-dependent decrease of Rt, with an $ED_{50}$ of 7.5×10⁻⁸ M (see FIG. 3 of U.S. patent application Ser. No. 08/598,852, filed Feb. 9, 1996).

C. Preparation and Purification of GST-ZOT

As a second ZOT fusion proteins a chimeric glutathione S-transferase (GST)-ZOT protein was expressed and purified.

More specifically, oligonucleotide primers were used to amplify the zot orf by polymerase chain reaction (PCR) using plasmid pBB241 (Baudry et al, supra) as template DNA. The forward primer (TCATCACGGC GCGCCAGG, SEQ ID NO:1) corresponded to nucleotides 15–32 of zot orf, and the reverse primer (GGAGGTCTAG AATCTGCCCG AT, SEQ ID NO:2) corresponded to the 5' end of ctxA orf. Therefore, amino acids 1–5 of ZOT were missing in the resulting fusion protein. The amplification product was inserted into the polylinker (SmaI site) located at the end of the GST gene in pGEX-2T (Pharmacia, Milwaukee, Wis.). pGEX-2T is a fusion-protein expression vector that expresses a cloned gene as a fusion protein with GST of *Schistosoma japonicum*. The fusion gene is under the control of the tac promoter. Upon induction with IPTG, derepression occurs and GST fusion protein is expressed.

The resulting recombinant plasmid, named pLC11, was electroporated in *E. coli* DH5α. In order to purify GST-ZOT fusion protein, 10 ml of Luria Bertani broth containing 100 μg/ml ampicillin were inoculated with a single colony containing pLC11, and incubated overnight at 37° C. with shaking. The culture was diluted 1:100 in 1.0 l of the same fresh medium and grown at 37° C. while shaking, to about 1.0×10⁸ cells/ml. 0.2 mM IPTG was then added to induce the GST-ZOT expression, and the culture was incubated at 37° C. for additional 3 hr. The bacteria were then pelleted, resuspended in 20 ml of ice cold PBS (pH 7.4) and lysed by the french press method. The GST-ZOT fusion protein was not soluble under these conditions as it sedimented with the bacterial pellet fraction. Therefore the pellet was resuspended in Laemli lysis buffer comprising 0.00625 M Tris-HCl (pH 6.8), 0.2 M 2-ME, 2.0% (w/v) SDS, 0.025% (w/v) bromophenol blue and 10% (v/v) glycerol, and subjected to electrophoresis on a 8.0% (w/v) PAGE-SDS gel, and stained with Coomassie brilliant blue. A band of about 70 kDa (26 kDa of GST+44 kDA of ZOT), corresponding to the fusion protein, was electroeluted from the gel using an electroseparation chamber (Schleicher & Schuell, Keene N.H.).

EXAMPLE 2

ZOT as a Nasal Absorption Enhancer

In view of the observation that tj represent universal structures that connect neighboring epithelial cells, it was postulated in the present invention that the permeability of epithelia of the nasal mucosa could be modulated by ZOT. This was confirmed by the following in vivo studies.

A. Animals and Reagents

Female Balb/c mice aged 6–8 weeks were obtained from Charles River (Calcoe Como, Italy).

LT-R72 is a mutant of *Escherichia coli* heat-labile enterotoxin (LT) containing the single mutations $Ala_{72} \rightarrow Arg$. This mutant was used as a control delivery enhancer.

Ovalbumin (Ova) was obtained from Sigma (St. Louis, Mo.).

MBP-ZOT was obtained as described in Example 1 above.

B. Immunization Schedule

Groups of five mice were immunized five times (days 0, 14, 21, 28, 35) intranasally with either:

(i) 5.0 µg of Ova alone, (ii) 1.0 µg of LT-R72, with and without 5.0 µg of Ova, or (iii) 0.1 µg or 1.0 µg of MBP-ZOT, with and without 5.0 µg of Ova.

Antigen (Ova) and adjuvant (LT or ZOT) were appropriately diluted in PBS, mixed together just before immunizations, and delivered with a Gilson pipette (15 µl/nostril) to partially anesthetized mice. The anesthetic was a mixture of 0.2 mg/ml xilazine and 5.0 mg/ml ketamine, and was given intraperitoneally (0.1 ml of mixture/10 g body weight).

C. Collection of Serum Samples

Serum samples were collected 24 hr before each immunization, and every week after the last immunization.

D. Collection of Nasal Washes

Nasal washes were collected 14 days after the fifth immunization. Lavages were performed on the sacrificed animal by repeated flushing and aspiration of 1.0 ml of PBS containing 0.1% (w/v) bovine serum albumin (BSA) and 1.0 mM PNSF (Fluka, Buchs, Switzerland) as protease inhibitor. The washes were stored at $-20°$ C.

E. ELISA Assay

To estimate the titer of Ova-specific antibodies, 96-well plates were coated with 0.1 ml of Ova (45 µg/ml). The plates were then washed with PBS containing 0.05% (v/v) Tween 20, and blocked for 1 hr at 37° C. with 0.2 ml of PBS containing 1.0% (w/v) BSA.

Serum samples from individual mice or pooled sera were serially diluted, starting from a 1:50 dilution, in PBS. Nasal washes (from individual mice or pooled animals) were serially diluted, starting from a 1:10 dilution, in PBS. The diluted samples were then added to the plates (0.1 ml/well), and incubated for 2 hr at 37° C. Next, the plates were washed with PBS containing 0.05% (v/v) Tween 20.

Plates containing serum samples were incubated with 0.1 ml of rabbit anti-mouse Ig horseradish peroxidase (HRP) conjugates (Dako, Glostrup, Denmark) diluted 1:2000 in PBS containing 0.1% (w/v) BSA and 0.025% (v/v) Tween 20, for 2 hr at 37° C.

Plates containing nasal washes were incubated with 0.1 ml of a-chain-specific biotin-conjugated goat anti-mouse serum (Sigma) diluted 1:1000 in PBS containing 0.1% (w/v) BSA and 0.025% (v/v) Tween 20, for 2 hr at 37° C. The plates were then washed with PBS containing 0.05% (v/v) Tween 20, and 0.1 ml of HRP-conjugated streptavidin (Dako, dilution 1.2000) was added for 2 hr at 37° C.

Antigen-bound antibodies for both the plates containing serum samples, and the plates containing nasal washes were visualized by adding o-phenylenediamine substrate (Sigma), and reading absorbance at 450 nm. Titers were determined arbitrarily as the reciprocal of the sample dilution corresponding to $OD_{450} = 0.3$. Serum samples and nasal washes with absorbance values lower than 0.3 above the background were considered negative.

F. Effect of ZOT and LT Mutants on Systemic Response to Ova

Previous studies have demonstrated that intranasal immunization with the non-toxic LT mutant LT-K63 induces a systemic response to Ova (Di Tommaso et al, *Infect. Immun.* 64:974–979 (1996)). LT-R72, a second LT mutant has been found to be even more immunogenic then LT-K63. However, LT-R72 has still been found to be reactogenic when tested in animal models. The mechanism by which both LT-K63 and LT-R72 induces this response has not been completely defined. However, the molecules seem to act as a mucosal adjuvant.

Figure 1:
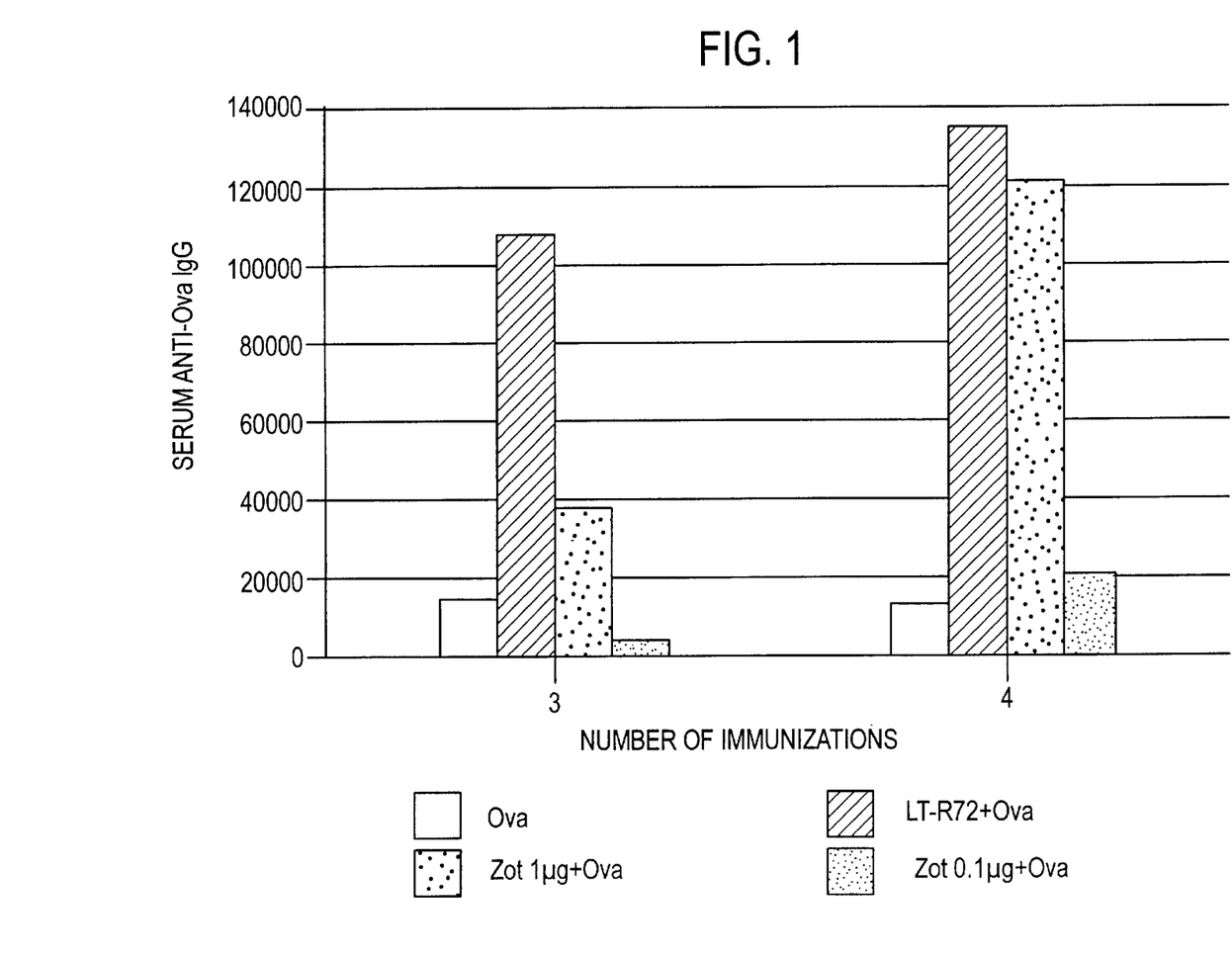
FIG. 1 shows the serum geometric titers of anti-Ova antibodies in mice treated with Ova alone (open bars), LT-R72+Ova (hatched bars), and ZOT+Ova (shaded bars).

Accordingly, the response to Ova in animals immunized intranasally with ZOT+Ova was compared to that obtained in animals immunized with either LT-R72+Ova or Ova alone. The results of the ELISA assay involving the serum samples, which are shown in FIG. 1, demonstrate that the animals immunized with ZOT+Ova developed a systemic response to Ova that was comparable to LT-R72, and significantly higher than compared to the animals challenged with Ova alone.

Figure 2A:
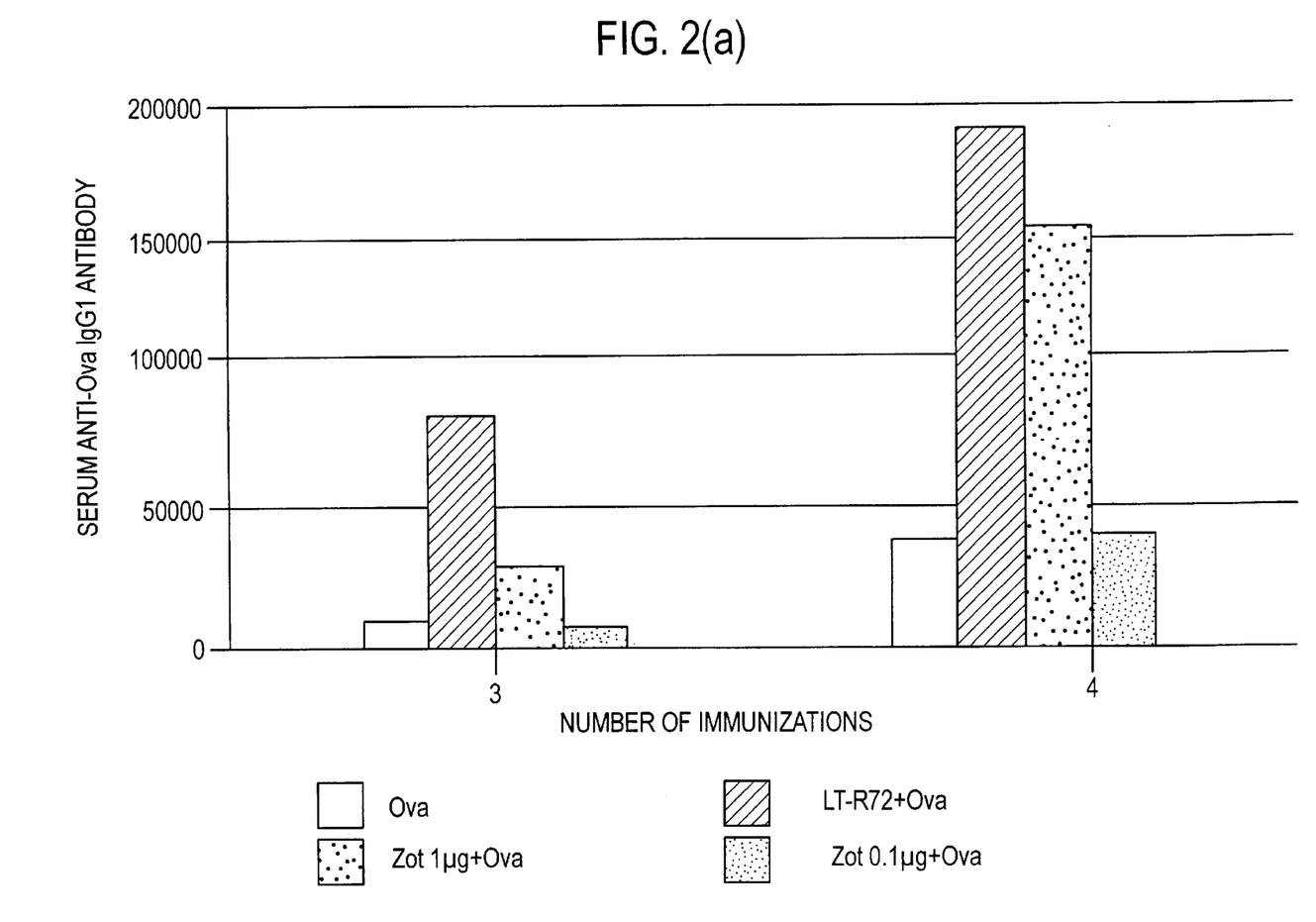
FIGS. 2A–2B show the serum anti-Ova IgG$_1$ (FIG. 2A) and IgG$_{2a}$ (FIG. 2B) antibody subclasses in mice treated with Ova alone (open bars), LT-R72+Ova (hatched bars), and ZOT+Ova (shaded bars).
Figure 2B:
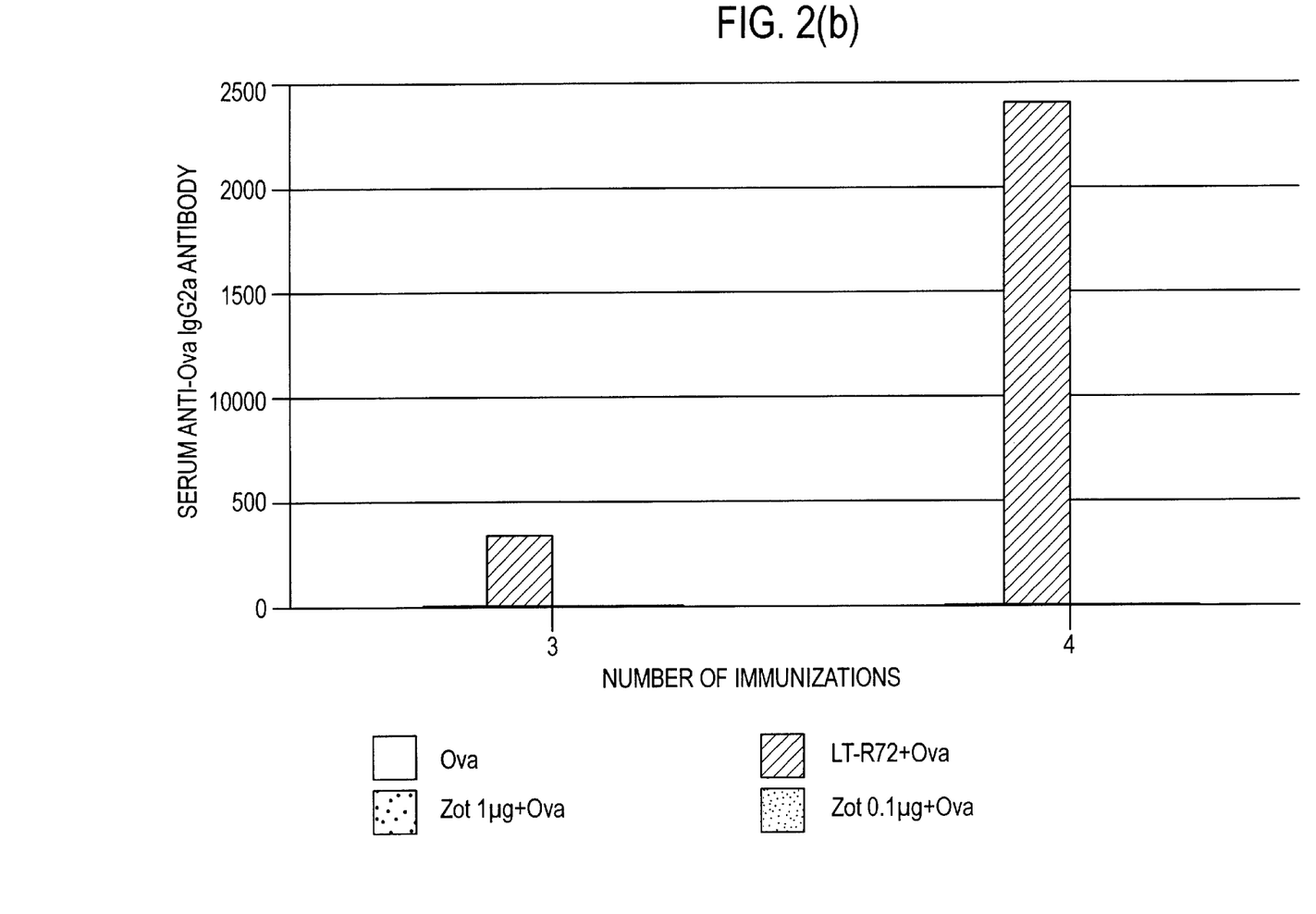

Evaluation of the anti-Ova IgG subclasses in the serum samples by an ELISA revealed that LT-R72 induced both a rise in $IgG_1$ (FIG. 2A) and $IgG_{2a}$, (FIG. 2B) antibodies, while ZOT-treated animals only showed an increase of the IgG, subclass (FIGS. 2A and 2B). These results suggest that the mechanisms of ZOT and LT-R72 antigen delivery are different, while their efficacy is comparable. A plausible hypothesis is that LT-R72 delivers antigens through the transcellular pathway (where the antigens may be partially modified by intracellular enzymes), while ZOT delivers antigens through the paracellular pathway.

ZOT and LT-R72 were also found to induce a mucosal immunoresponse, as determined by the elevated secretory IgA titer detected in the ELISA assay of the nasal washes of mice treated with either ZOT+Ova or LT-R72+Ova (see FIG. 3).

The above results demonstrate that ZOT can enhance the nasal delivery of proteins, as a prototype therapeutic agent.

While the invention has been described in detail, and with reference to specific embodiments thereof, it will be apparent to one of ordinary skill in the art that various changes and modifications can be made therein without departing from the spirit and scope thereof.

---

What is claimed:

1. A nasal dosage composition for nasal delivery comprising:
   (A) a therapeutic agent; and
   (B) a nasal absorption enhancing effective amount of purified *Vibrio cholera* zonula occludens toxin.

2. The nasal dosage composition of claim 1, wherein said therapeutic agent is selected from the group consisting of a drug compound, biologically active peptide and vaccine.

3. The nasal dosage composition of claim 2, wherein said drug compound is selected from the group consisting of a drug which acts on the cardiovascular system, a drug which acts on the central nervous system, an antineoplastic drug and antibiotics.

4. The nasal dosage composition of claim 3, wherein said drug which acts on the cardiovascular system is selected from the group consisting of lidocaine, adenosine, dobutamine, dopamine, epinephrine, norepinephrine and phentolamine.

5. The nasal dosage composition of claim 3, wherein said drug which acts on the central nervous system is selected from the group consisting of doxapram, alfentanil, dezocin, nalbuphine, buprenorphine, naloxone, ketorolac, midazolam, propofol, metacurine, mivacurium and succinylcholine.

6. The nasal dosage composition of claim 3, wherein said antineoplastic drug is selected from the group consisting of cytarabine, mitomycin, doxorubicin, vincristine and vinblastine.

7. The nasal dosage composition of claim 3, wherein said antibiotic is selected from the group consisting of methicillin, mezlocillin, piperacillin, cetoxitin, cefonicid, cefmetazole and aztreonam.

8. The nasal dosage composition of claim 2, wherein said biologically active peptide is selected from the group consisting of a hormone, lymphokine, globulin and albumin.

9. The nasal dosage composition of claim 8, wherein said hormone is selected from the group consisting of testosterone, nandrolene, menotropins, progesterone, insulin and urofolltropin.

10. The nasal dosage composition of claim 8, wherein said lymphokine is selected from the group consisting of interferon-$\alpha$, interferon-$\beta$, interferon-$\gamma$, interleukin-1, interleukin-2, interleukin-4 and interleukin-8.

11. The nasal dosage composition of claim 8, wherein said globulin is an immunoglobulin selected from the group consisting of polyvalent IgG, and specific IgG, IgA or IgM.

12. The nasal dosage composition of claim 1, wherein the ratio of therapeutic agent to zonula occludens toxin is in the range of about 1:10 to 3.1.

13. The nasal dosage composition of claim 12, wherein the ratio of therapeutic agent to zonula occludens toxin is in the range of about 1:5 to 3:1.

14. The nasal dosage composition of claim 1, wherein zonula occludens toxin is present in the composition in an amount of from about 40 ng to 1000 ng.

15. The nasal dosage composition of claim 14, wherein zonula occludens toxin is present in the composition in an amount of from about 400 ng to 800 ng.

16. A method for nasal delivery of a biological ingredient comprising administering a nasal dosage composition for nasal delivery of a therapeutic agent comprising:
   (A) a therapeutic agent; and
   (B) an nasal absorption enhancing effective amount of purified *Vibrio cholera* zonula occludens toxin.

17. The method of claim 16, wherein said therapeutic agent is selected from the group consisting of a drug compound, biologically active peptide and vaccine.

18. The method of claim 17, wherein said drug compound is selected from the group consisting of a drug which acts on the cardiovascular system, a drug which acts on the central nervous system, an antineoplastic drug and antibiotics.

19. The method of claim 18, wherein said drug which acts on the cardiovascular system is selected from the group consisting of lidocaine, adenosine, dobutamine, dopamine, epinephrine, norepinephrine and phentolamine.

20. The method of claim 18, wherein said drug which acts on the central nervous system is selected from the group consisting of doxapram, alfentanil, dezocin, nalbuphine, buprenorphine, naloxone, ketorolac, midazolam, propofol, metacurine, mivacurium and succinylcholine.

21. The method of claim 18, wherein said antineoplastic drug is selected from the group consisting of cytarabine, mitomycin, doxorubicin, vincristine and vinblastine.

22. The method of claim 18, wherein said antibiotic is selected from the group consisting of methicillin, mezlocillin, piperacillin, cetoxitin, cefonicid, cefmetazole and aztreonam.

23. The method of claim 17, wherein said biologically active peptide is selected from the group consisting of a hormone, lymphokeine, globulin and albumin.

24. The method of claim 23, wherein said hormone is selected from the group consisting of testosterone, nandrolene, menotropins, insulin and urofolltropin.

25. The method of claim 23, wherein said lymphokine is selected from the group consisting of interferon-α, interferon-β, interferon-γ, interleukin-1, interleukin-2, interleukin-4 and interleukin-8.

26. The method of claim 23, wherein said globulin is an immunoglobulin selected from the group consisting of polyvalent IgG, and specific IgG, IgA or Igm.

27. The method of claim 16, wherein the ratio of therapeutic agent to zonula occludens toxin is in the range of about 1:10 to 3:1.

28. The method of claim 27, wherein the ratio of therapeutic agent to zonula occludens toxin is in the range of about 1:5 to 2:1.

29. The method of claim 16, wherein zonula occludens toxin is present in the composition in an amount of from about 40 ng to 1000 ng.

30. The method of claim 29, wherein zonula occludens toxin is present in the composition in an amount of from about 400 ng to 800 ng.

31. The method of claim 16, wherein the zonula occludens toxin is administered in an amount such that the final concentration in the nose is in the range of about $10^{-5}$ M to $10^{-10}$ M.

32. The method of claim 31, wherein the zonula occludens toxin is administered in an amount such that the final concentration in the nose is in the range of about $10^{-6}$ M to $5.0 \times 10^{-8}$ M.

* * * * *

UNITED STATES PATENT AND TRADEMARK OFFICE
CERTIFICATE OF CORRECTION

PATENT NO.   : 5,908,825
DATED        : June 1, 1999
INVENTOR(S)  : Alessio Fasano, et al It is certified that error appears in the above-indentified patent and that said Letters Patent is hereby corrected as shown below:

In Column 1, lines 5-6, delete in its entirety, and insert therefor

-- The development of the present invention was supported by the University of Maryland, Baltimore, Maryland and by funding from the National Institute of Health (NIH AI35740; NIH DK 48373 and NIH AI19716). The Government has certain rights. --.

Signed and Sealed this

Twelfth Day of October, 1999

Attest:

Attesting Officer

Q. TODD DICKINSON

Acting Commissioner of Patents and Trademarks